United States Patent [19]

Shinkai et al.

[11] Patent Number: 4,829,082

[45] Date of Patent: May 9, 1989

[54] PHARMACEUTICAL COMPOSITIONS FOR THE TREATMENT OF SKIN DISEASES

[75] Inventors: Hiroshi Shinkai, Ohita; Takao Kishiye, Kamifukuoka, both of Japan

[73] Assignee: Nisshin Chemicals Co., Ltd., Japan

[21] Appl. No.: 902,299

[22] Filed: Aug. 29, 1986

[51] Int. Cl.$^4$ ............................................. A61K 31/355
[52] U.S. Cl. .................................... 514/458; 514/725; 514/928
[58] Field of Search ........................ 514/725, 458, 928

[56] References Cited

U.S. PATENT DOCUMENTS 3,878,202  4/1975  Kukawa et al. ..................... 549/410

FOREIGN PATENT DOCUMENTS 1466062  3/1977  United Kingdom .

OTHER PUBLICATIONS

Thomas et al. J. of the Am. Acad. Dermatol., vol. 4, No. 5, pp. 505–513 (1981).

Primary Examiner—Leonard Schenkman
Attorney, Agent, or Firm—Abelman Frayne Rezac & Schwab

[57] ABSTRACT

This invention relates to pharmaceutical compositions for the treatment of skin diseases which comprises as an active ingredient vitamin A esters of α-tocopherol.

2 Claims, No Drawings

PHARMACEUTICAL COMPOSITIONS FOR THE TREATMENT OF SKIN DISEASES

BACKGROUND OF THE INVENTION

1. Field of the Invention

This invention relates to pharmaceutical compositions for the treatment of skin diseases.

2. Discussion of the Prior Art

Generally, skin diseases include dermatitis whose principal symptom is inflammation of the skin, dermal ulcer causing rupture of the skin, skin keratosis showing abnormality in constituents for constituting the skin, and any disease of the skin caused by abnormal secretion and microorganism or parasites.

External preparations which have heretofore been used widely in the treatment of these skin diseases include zinc oxide ointments, adrenocortical hormone containing ointments, non-steroid antiphlogistic containing ointments, and antibiotic containing ointments.

Of these prior external preparations, the adrenocortical hormone containing ointments have markedly high therapeutic effects, but the degree and frequency of the adverse side effects are high and a rebound phenomenon is often observed. Furthermore, external preparations such as zinc oxide ointments are insufficient in therapeutic effects, but with minimal adverse side effects. In general, expected effects are difficult to attain by the use of these ointments when patients are suffering, in addition to skin diseases, from generalized diseases such as diabetes and rheumatism.

Particularly, no suitable external preparations for use in the treatment of bedsore, i.e., a dermal ulcer caused by such physical stimuli as pressure, have heretofore been found, and excellent pharmaceutical preparations for the treatment intended are demanded (cf. Shozaburo Nomachi et al. "Pharmacology and Treatment", 10, 10, 5793 (1982)). There is need for a measure to improve the state or condition of the diseases which require no operational means or which are unable to undergo operation.

SUMMARY OF THE INVENTION

The present invention results from efforts to develop new pharmaceutical compositions with minimal side effects that could be more effective in treating skin diseases than presently available drugs.

More particularly, the invention relates to pharmaceutical compositions for the treatment of skin-diseases which comprise as an active ingredient vitamin A acid esters of α-tocopherol which is referred hereafter as "TOC ester".

"TOC ester" used in the present invention is a known compound having its chemical name of tocopheryl retinoate as disclosed in U.S. Pat. No. 3,878,202. Of TOC ester, α-tocopherol refers to DL-α-tocopherol, D-α-tocopherol and natural mixed tocopherol containing D-α-tocopherol, and vitamin A acid refers to trans or cisretinoic acid.

TOC ester is extremely low in toxicity and moreover has almost no side effects.

Acute toxicity in mice

| Route of Administration | LD$_{50}$ (mg/kg) |
| --- | --- |
| Oral | >10,000 |
| Subcutaneous | >2,500 |
| Intramascular | >2,500 |
| Intraperitoneal | >10,000 |

Percutaneous subacute toxicity in rats

Tests were conducted for 30 days using lotions containing 0.5% and 1.5% of TOC ester, respectively. During experiments, there was no change in general symptoms, dermal symptoms and body weight, and also no change was observed at all in blood and physiological examinations, anatomical observation, wet weight of organs, and pathological histological examination conducted after completion of the test.

Appearance of skin allergy in guinea pigs

Induction tests were conducted, wherein guinea pigs were sensitized with 0.1 ml of 30% chloroform solution, and two weeks after sensitization, the pigs were treated on the skin with 0.1 ml of acetone solution containing 0.05%, 0.10% and 0.20% of TOC ester, respectively. No contact skin allergy was observed.

Irritation on eyes of rabbits

Irritation tests were conducted using physiological salt suspensions containing 0.05% and 0.5% of TOC ester, respectively, whereupon no change was observed.

Chafe on human being (Patch test)

Tests were conducted using cream containing 0.1% and 0.3% of TOC ester, respectively, whereupon no rubor or expansion was observed at all.

In the present invention, TOC ester is formulated into dosage forms useful for the treatment of skin diseases, for example, ointments, lotions, liniments and aerosols. The above-mentioned topical application forms of the present composition can be prepared by using usual ingredients for such preparations for topical application. Though no strict limitation is placed, the amount of TOC ester to be contained in these dosage forms is about 0.01–10% by weight, preferably about 0.1–5% by weight.

The above-mentioned dosage forms may be prepared according to any conventional methods. For instance, in preparing ointments, TOC esters and suitably selected constituents selected from other materials are subjected to processing steps such as mixing, emulsifying and dispersing. Other materials include oily substances, for example, liquid paraffin, vaseline, silicone oil, aliphatic higher alcohols, higher fatty acids, fatty acid esters, vegetable oils, castor oil, lanoline and its derivatives, squalene, and squalane; emulsifiers and dispersants, for example, polyhydric alcohol ester type nonionic surfactants and polyoxyethylene type nonionic surfactants; wetting agents, for example, glycerol, propylene glycol, sorbitol and amino acids; stabilizers, for example, antioxidants, and preservatives; and others, for example, polyethylene glycol, polyethylene, and suspending agents. Lotions may be in the form of suspension, emulsion and solution and they are prepared according to any conventional methods using suspending agents, emulsifiers and solvents, respectively. Aerosols include liquefied gas type compressed gas type and the like. Preferred aerosols are liquefied gas type in o/w emulsion of three phases.

The pharmaceutical compositions of the present invention are effective in the treatment of various skin diseases due to the loss of the epidermis, dermis and subcutis, for example, bedsore, burn ulcer, dermal ulcer occurred in rheumatic patient, frostbite, zoster, skin pruritus, skin keratosis, callosity, eczema craquelé, and housewife eczema. The present pharmaceutical compositions are applied or sprayed one to several times a day directly to affected skin or mucous membrane, or are used after applying or spraying them on a fabric or gauze. The dosage applied will, of course, vary depending upon nature and extent of symptoms and the largeness of affected area.

The following examples will serve to further illustrate the nature of the present invention without being a limitation on the scope thereof, the scope being defined solely by the appended claims.

EXAMPLE 1

(Oil ointment)

In a stainless steel vessel, 900 g of white vaselin and 95 g of purified lanolin were melt under heat and stirred. After cooling the melt to 40–50° C., 5 g of TOC ester were added and thoroughly stirred to prepare an ointment containing 0.5% of TOC ester.

EXAMPLE 2

(Lotion)

12 g of propylene glycol were added to 0.3 g of TOC ester and stirred and made up 100 ml by the addition of purified water. The mixture was homogeneously dispered by means of supersonic wave to prepare a lotion containing 0.3% of TOC ester.

EXAMPLE 3

(Hydrophilic ointment)

997 g of a hydrophilic ointment base (Japanese Pharmacopoeia) were placed into a stainless steel vessel, heated to about 75° C. and melt. After cooling the melt to 40°–50° C., 3 g of TOC ester were added and thoroughly stirred to prepare a hydrophilic ointment containing 0.3% of TOC ester.

To detect the therapeutic effects of the pharmaceutical compositions, a test was made on rabbits and human beings. The results are shown hereinbelow.

TEST EXAMPLE 1

(Experimental bedsore of rabbits)

Japanese white male rabbits weighing 2.5–4.4 kg were used.

An experimental bedsore was formed on the rabbits in accordance with the methods of Kosiak (Arch. Phys. Med. Rehabil., Vbl. 40, 62–69, 1959) and Fukawa et al. (Applied Pharmacology, Vol. 23, No. 6, 999–1011, 1982). The rabbits were anethetized with Nembutal® and fixed so that the shaved right trochanteric region of the rabbits was held horizontally, a pressure of 500–600 mmHg/cm$^2$ was applied to 2 cm$^2$ area of the skin in the shaved region, and the rabbits were held for 5–10 hours to allow development of bedsore. Two days after application of the pressure, occurrence of bedsore was confirmed.

The affective rabbits were distributed to two groups. One group (5 rabbits) was coated on the surface of bedsore region with a lotion containing 0.5% by weight of TOC ester by a brush once a day (said lotion being prepared from 900 parts by weight of water, 95 parts by weight of ethanol and 5 parts by weight of TOC ester). The other control group (4 rabbits) was coated once a day with only the base of the lotion (mixture of 900 parts of weight of water and 95 parts by weight of ethanol). One week after the treatment, a sheet of Japanese paper was applied to the bedsore area occurred in each rabbit. The injured area of said bedsore was transferred to the paper according to the etching method, and the transferred areas were measured by means of a planimeter. As shown in the following table, marked reduction in the injured area of bedsore was observed on the group (5 rabbits) to which the lotion containing 0.5% by weight of TOC ester was applied.

| Tested Lotion | Injured area (cm2) | | | Average ± standard deviation |
|---|---|---|---|---|
| | At the initiation of treatment | After one week | Difference | |
| TOC ester 0.5% group | 2.68 | 1.30 | 1.38 | 1.82 ± 0.213 |
| | 3.01 | 0.98 | 2.03 | |
| | 1.95 | 0.70 | 1.25 | |
| | 2.20 | 0.09 | 2.11 | |
| | 2.56 | 0.23 | 2.33 | |
| Control group | 2.01 | 1.51 | 0.50 | 0.907 ± 0.292 |
| | 1.87 | 0.90 | 0.97 | |
| | 2.43 | 1.98 | 0.45 | |
| | 3.15 | 1.44 | 1.71 | |

TEST EXAMPLE 2

(Bedsore)

An oil ointment containing 0.5% by weight of TOC ester spread on a gauze was applied to the bedsore areas occurred in the ischium and whirlbone of a male of thirty-six years old lying in bed for a long time suffering from injury of myelon, said gauze being embedded in a depressed region of deep ulcer of bedsore after crumpling the gauze into a ball, and being applied as it was to a superficial region of the ulcer. The gauze was exchanged once or twice a day. After one week from the treatment, epidermization was observed on the superficial region of ulcer. Two weeks thereafter, sore disappeared from the superficial region of ulcer, and the epidermis was formed to close the sore region. About one month after the treatment, there was observed marked buildup of flesh owing to granulation at the bottom region of deep ulcer, and a remarkable improvement in cuticularization was seen over about 5 mm in width along the circumference of ulcer.

TEST EXAMPLE 3

(Dermal ulcer occurred in a rheumatic patient)

The same ointment as used in Test Example 2 was applied directly or applied using a gauze over which said ointment had been spread, to a dermal ulcer occurred on a sacral region, sciatic tuber region, elbow head, inner and outer ankle regions and heel region of a female of twenty-seven years old suffering from arthrorheumatism under hospital treatment. There were observed marked improvements in proliferation of the granulation and in epidermization in about two weeks in the case of small ulcers and in about three months in the case of large ulcers. No adverse side effects was observed during that treatment period.

TEST EXAMPLE 4

(Burn ulcer)

The same ointment as used in Test Example 2 was applied directly or applied using a gauze over which said ointment had been spread, to an inveterate burn ulcer occurred on the ankle and crus of a male of sixty-nine years old lying in bed suffering from injury of myelon, whereupon a remarkable improvement in healing of the ulcer was observed after one week from the treatment.

TEST EXAMPLE 5

(Frostbite)

The same ointment as used in Test Example 2 was applied directly to the fingers affected by frostbite of a female of twenty-two years old, whereupon an improvement in healing of frostbite was observed in about one week.

TEST EXAMPLE 6

(Zoster)

To an ulcer produced after zoster had occurred on the neck through the shoulder of a male of seventy-six years old was applied a gauze over which the same ointment as used in Test Example 2 had been spread. There was observed a marked improvement in healing of the ulcer about one week after the treatment. Moreover, no recurrence was observed even after the lapse of six months after the healing.

TEST EXAMPLE 7

(Skin pruritus)

The same ointment as used in Test Example 2 was applied directly to the sore produced by scratches on the breast and arms of a male of sixty-five years old, whereupon itching sensation ceased one day after treatment and the skin pruritus healed perfectly following disappearance of the sore three days after the treatment.

TEST EXAMPLE 8

(Skin keratosis)

To the skin keratosis occurred on the arms and crus of a female of thirty-three years old was applied directly the same ointment as used in Test Example 2, whereupon a marked improvement in healing of the disease was observed three days after treatment.

TEST EXAMPLE 9

(Callosity)

The lotion containing 0.5% by weight of TOC ester was applied to a callosity occurred on the sole of a foot of a male of thrity-nine years old, whereupon an improvement such as softening of the callosity was observed about two weeks after treatment.

TEST EXAMPLE 10

[Eczema craquelé (cracking and chaps)]

The hydrophilic ointment containing 0.3% by weight of TOC ester was applied directly to the eczema craquelé (cracking and chaps) on both hands of a female of fifty-five years old, whereupon a marked improvement in healing of the disease was observed one month after treatment and the disease perfectly healed two months after the treatment. Moreover, no adverse side-effects were observed during the period of treatment.

TEST EXAMPLE 11

(Housewife eczema)

To the housewife eczema occurred on both hands of a female of forty-seven years old was applied the same hydrophilic ointment as used in Test Example 10, whereupon a marked improvement in healing of the disease was observed in a week.

As is clear from the therapeutic results as mentioned above, the present pharmaceutical compositions are extremely low in toxicity and exhibit remarkable healing effect on a variety of skin diseases. Furthermore, the present pharmaceutical compositions are of an advantage of no adverse side effects.

What is claimed is:

1. A method of treatment of skin diseases due to the loss of the epidermis and dermis which comprises topically applying an effective amount of Vitamin A acid esters of α-tocopherol in a pharmaceutically acceptable carrier to the affected, and if necessary, surrounding area of the skin.

2. A method of treatment of skin diseases due to the loss of the epidermis and dermis according to claim 1, which comprises bedsore, burn, ulcer, dermal ulcer occurring in rheumatic patients, frostbite and zoster.

* * * * *